(12) United States Patent
Hara et al.

(10) Patent No.: US 12,360,032 B2
(45) Date of Patent: Jul. 15, 2025

(54) PERMEATION ESTIMATION APPARATUS AND PERMEATION ESTIMATION METHOD

(71) Applicant: Yokogawa Electric Corporation, Tokyo (JP)

(72) Inventors: Risa Hara, Musashino (JP); Kodai Murayama, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 241 days.

(21) Appl. No.: 17/999,309

(22) PCT Filed: May 21, 2021

(86) PCT No.: PCT/JP2021/019475
§ 371 (c)(1),
(2) Date: Nov. 18, 2022

(87) PCT Pub. No.: WO2021/235555
PCT Pub. Date: Nov. 25, 2021

(65) Prior Publication Data
US 2023/0184660 A1    Jun. 15, 2023

(30) Foreign Application Priority Data

May 22, 2020  (JP) .................................. 2020-089588

(51) Int. Cl.
*G01N 15/08*  (2006.01)
(52) U.S. Cl.
CPC ..... *G01N 15/08* (2013.01); *G01N 2015/0846* (2013.01)

(58) Field of Classification Search
None
See application file for complete search history.

(56) References Cited

U.S. PATENT DOCUMENTS 4,538,460 A    9/1985  Schettler, Jr.

FOREIGN PATENT DOCUMENTS

| JP | 2003-235544 A | 8/2003 |
|---|---|---|
| JP | 2008203156 A | 9/2008 |
| JP | 2015-216886 A | 12/2015 |
| JP | 2019-162052 A | 9/2019 |

OTHER PUBLICATIONS

Asano et al., "Exuding Behavior of Soybean Oligosaccharides by Hot Water Immersing", Journal of the Japanese Society for Food Science and Technology, 1991, vol. 38, No. 9, pp. 770-775; English abstract; Cited in Specification.
(Continued)

*Primary Examiner* — Alexander A Mercado
(74) *Attorney, Agent, or Firm* — RANKIN, HILL & CLARK LLP

(57) ABSTRACT

A permeation estimation apparatus includes an interface configured to connect to a sensor that measures a concentration of a component, of a soaked material, that is eluted in a soaking solution in which the soaked material is soaking, and a controller configured to acquire the concentration of the component from the interface and estimate the degree of permeation of the soaking solution with respect to the soaked material based on the measurement result of the concentration of the component.

8 Claims, 8 Drawing Sheets

(56) References Cited

OTHER PUBLICATIONS

Wanaga et al., "Stabilization of Soybean Oil Bodies Using Protective Pectin Coatings Formed by Electrostatic Deposition", Journal of Agricultural and Food Chemistry, 2008, 56, pp. 2240-2245; Cited in Specification.
Extended European Search Report (EESR) dated May 23, 2024 for European Patent Application No. 21809621.2.
Chinese Office Action dated Mar. 22, 2025 for Chinese Patent Application No. 202180035719.7; English translation.

PERMEATION ESTIMATION APPARATUS AND PERMEATION ESTIMATION METHOD

CROSS-REFERENCE TO RELATED APPLICATION

The present application claims priority to Japanese Patent Application No. 2020-89588 filed on May 22, 2020, the entire contents of which are incorporated herein by reference.

TECHNICAL FIELD

The present disclosure relates to a permeation estimation apparatus and a permeation estimation method.

BACKGROUND

It is known that a suitable treatment time exists for the soaking treatment of beans. For example, see Patent Literature (PTL) 1.

CITATION LIST

Patent Literature

PTL 1: JP 2019-162052A

SUMMARY

Technical Problem

The relationship between the degree of permeation of water into beans and the soaking time varies depending on the condition of the beans before treatment. In other words, the suitable treatment time in the soaking treatment varies depending on the condition of the beans before treatment. To determine the treatment time, the condition of the soaked material during the soaking treatment must be monitored.

The present disclosure has been conceived in light of this point and aims to provide a permeation estimation apparatus and a permeation estimation method that can monitor the condition of a soaked material during soaking treatment.

Solution to Problem

A permeation estimation apparatus according to some embodiments includes an interface configured to connect to a sensor that measures a concentration of a component, of a soaked material, that is eluted in a soaking solution in which the soaked material is soaking; and a controller configured to acquire the concentration of the component from the interface and estimate a degree of permeation of the soaking solution with respect to the soaked material based on a measurement result of the concentration of the component. In this way, the condition of the soaked material is quantitatively evaluated. Consequently, the condition of the soaked material during the soaking treatment can be easily monitored.

In the permeation estimation apparatus according to an embodiment, in a case in which an estimated value of the degree of permeation is within a predetermined range, the controller may be configured to determine a timing for ending a process of soaking the soaked material in the soaking solution. In this way, the timing for ending is determined based on a quantitative evaluation. Consequently, the accuracy of estimating the timing for ending the soaking treatment is improved.

In the permeation estimation apparatus according to an embodiment, based on an estimated value of the degree of permeation, the controller may be configured to estimate a quality of a processed product obtainable by processing the soaked material. In this way, the timing for ending the soaking treatment is determined while taking into consideration the quality of the processed product. Consequently, the accuracy of estimating the timing for ending the soaking treatment is improved.

In the permeation estimation apparatus according to an embodiment, based on an estimated value of the degree of permeation, the controller may be configured to determine a processing condition of the soaked material in a process subsequent to a soaking process. In this way, the quality of the processed product can be adjusted according to the condition of the soaked material during the soaking process. Consequently, the degree of freedom of the timing for ending the soaking treatment is increased.

A permeation estimation method according to some embodiments includes acquiring a measurement result of a concentration of a component of a soaked material from a sensor that measures the concentration of the component, the component being eluted in a soaking solution in which the soaked material is soaking; and estimating a degree of permeation of the soaking solution with respect to the soaked material based on a measurement result of the concentration of the component. In this way, the condition of the soaked material can be evaluated quantitatively. Consequently, the condition of the soaked material during the soaking treatment can be easily monitored.

Advantageous Effect

According to the present disclosure, a permeation estimation apparatus and a permeation estimation method that can monitor the condition of a soaked material during soaking treatment are provided.

DETAILED DESCRIPTION

Figure 1:
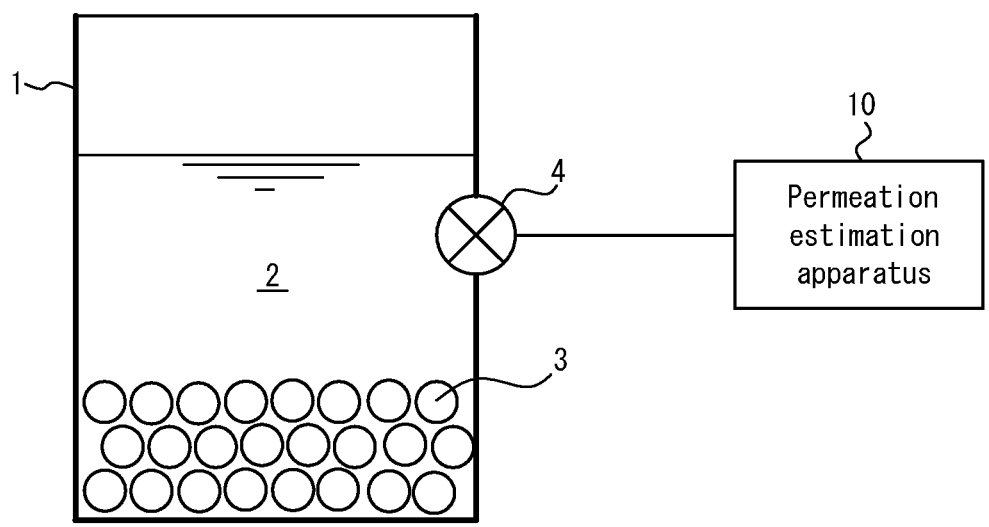
FIG. 1 illustrates an example configuration of a soaking treatment system.

In the manufacturing process of soybean products such as tofu, soymilk, or boiled soybeans, a process of soaking soybeans in water is performed to facilitate the extraction of components in soybeans and to improve the taste of food products. The process of soaking soybeans in water is also referred to as a soaking process. For example, soymilk is produced by soaking soybeans in water and then crushing, adding water, heating, and filtering. It is reported in Reference 1 below that the quality of the soymilk produced varies depending on the soaking time of the soybeans.

Reference 1: Journal of the Japanese Society for Food Science and Technology, Vol. 38, No. 9, 770-775, (1991)

Several quality control conditions are known for the soaking process, including soaking time, water temperature, and soybean swelling ratio. Here, as a comparative example, the soaking time could be controlled in the range of 5 to 48 hours as a guideline, or the water absorption could be controlled in the range of 180% to 240% as a guideline. In practice, the soaking conditions are determined by rule of thumb by the operators at each production site. The end point of soaking is determined based on the feel of the soybeans when touched by hand (such as the degree of peeling or elasticity), the color, the presence of a core inside cracked soybeans, or the weight or size of the soybeans and other indicators. The indicators for judgment by touch or visual inspection of the soybeans are based on the five human senses, making quantitative judgment difficult. Furthermore, this judgment method is not necessarily applicable to all soybeans due to individual differences among soybeans. It is also difficult for a skilled person to hand down this sense to a non-skilled person.

Table 1 below lists an example of the change in weight and size of soybeans before and after soaking as an example of data used to determine the end point of soaking. The entry "n =10" in the soybean size column means that the soybean size is calculated as the average of 10 soybeans.

TABLE 1

| Soaking time | Soybean weight (g) Before soaking | Soybean weight (g) After soaking | Swelling ratio | Size (mm), n = 10 Before soaking | Size (mm), n = 10 After soaking | Raw soymilk component concentration Lipid | Raw soymilk component concentration Protein |
|---|---|---|---|---|---|---|---|
| 2 hours | 9.97 | 15.32 | 1.54 | 9.0 × 8.5 | 12.1 × 9.8 | low | low |
| 9 hours | 10.14 | 22.42 | 2.21 | | 16.0 × 9.8 | high | high |
| 24 hours | 9.92 | 22.50 | 2.27 | | 16.1 × 10.3 | high | high |

When the soaking time is 2 hours, the swelling ratio before and after soaking and the size after soaking are clearly smaller than when the soaking time is 9 hours or 24 hours. It can thus be said that water has not sufficiently permeated into the soybeans. Soybeans soaked for 2 hours do not sufficiently crush as a result of water not having sufficiently penetrated into the soybeans. Therefore, the lipid and protein concentrations of the raw soymilk obtained from soybeans with a soaking time of 2 hours are low. In other words, the soybean component concentration in the raw soymilk is low.

On the other hand, when the soaking time is 9 hours or 24 hours, the swelling ratio before and after soaking and the size after soaking are clearly larger than when the soaking time is 2 hours. It can thus be said that water has sufficiently permeated the soybeans to the point of saturation.

When the soaking time is 24 hours, the lipid and protein concentrations of the raw soymilk are nearly unchanged compared to when the soaking time is 9 hours. In other words, 24 hours is an excessively long soaking time.

However, the difference in soybean size between a soaking time of 9 hours and a soaking time of 24 hours is small. Therefore, it is difficult to determine whether the soaking time is appropriate based on how large soybeans appear to be. In the case of determining the soaking time based solely on how large the soybeans appear to be, the soybeans may consequently be left soaking for too long.

It is reported in the above-described Reference 1 that soybean components, such as oligosaccharides, are eluted into the water in which the soybeans are soaked during the soaking process. It is also reported in 2, described below, that sugar contributes to the dispersion of lipids or proteins in soymilk. In light of these references, lipids and proteins are separated from water and precipitated by agglomeration, which significantly affects the shape retention of processed soybean products such as juice drinks or gelato.

Reference 2: Journal of Agricultural and Food Chemistry. 2008, 56, 2240-2245.

The determination to end the soaking process in the above-described comparative example has the following issues.

(1) For example, it is difficult to determine the end point of soaking quantitatively when a person confirms the sensation of touching the soybeans (such as the degree of peeling or elasticity), the presence of a core inside cracked soybeans, or the appearance (such as color) using the five human senses.

(2) It is difficult to determine the end point of soaking based on the weight or size of the soybeans. This is because the difference in soybean swelling ratio or soybean size between a suitable soaking time and an excessively long soaking time is minimal. In the case of monitoring only the weight or size of the soybeans, the soaking process may be left to continue even when the soaking time has become excessively long.

(3) If the end point of soaking is in fact determined by either of the above methods (1) or (2), there is a risk that product quality will degrade or soybean lots will be discarded as a result of the end point of soaking being incorrectly determined.

(4) The time required to produce soy products may also increase.

(5) Another possible method could be to split the soybeans to evaluate the inside, but this method would incur the loss of some of the soybeans used to make soybean products.

To address these issues, the present disclosure describes a soaking treatment system that includes a permeation estimation apparatus 10 (see FIG. 1 and other drawings) that can improve the accuracy of estimating the timing for ending the soaking process.

(Embodiment of the Present Disclosure)

As illustrated in FIG. 1, a soaking treatment system according to the present disclosure includes a permeation estimation apparatus 10 and a water tank 1. The water tank 1 stores a soaking solution 2, which is water in which a soaked material 3 is soaked. The water tank 1 further includes a sensor 4 that detects components dissolved in the soaking solution 2.

The soaked material 3 may, for example, be soybeans but is not limited thereto and may be various other items as described below. The soaking solution 2 may, for example, be water but is not limited thereto and may be various other liquids. The temperature of the soaking solution 2 may be room temperature (such as 20° C. to 25° C.) or may be lower or higher than room temperature.

The sensor 4 may, for example, be configured to include a near-infrared sensor, a Raman sensor, a refractometer, or a BRIX meter. Near-infrared sensors and Raman sensors can measure the concentration of each type of target, such as sugar (carbohydrates), protein, or fat, by detecting the difference in absorption rate that varies by molecular weight of the target. Refractometers and BRIX meters cannot measure the concentration by type but can measure the combined concentration of all components dissolved in the soaking solution 2.

In the soaking treatment system, the sensor 4 may be installed to directly measure the soaking solution 2 stored in the water tank 1. The soaking treatment system may be configured to sample and measure the soaking solution 2 from the water tank 1. Methods for sampling and measuring the soaking solution 2 may include ultraviolet or visible spectroscopy, ether extraction, or the like.

Figure 2:
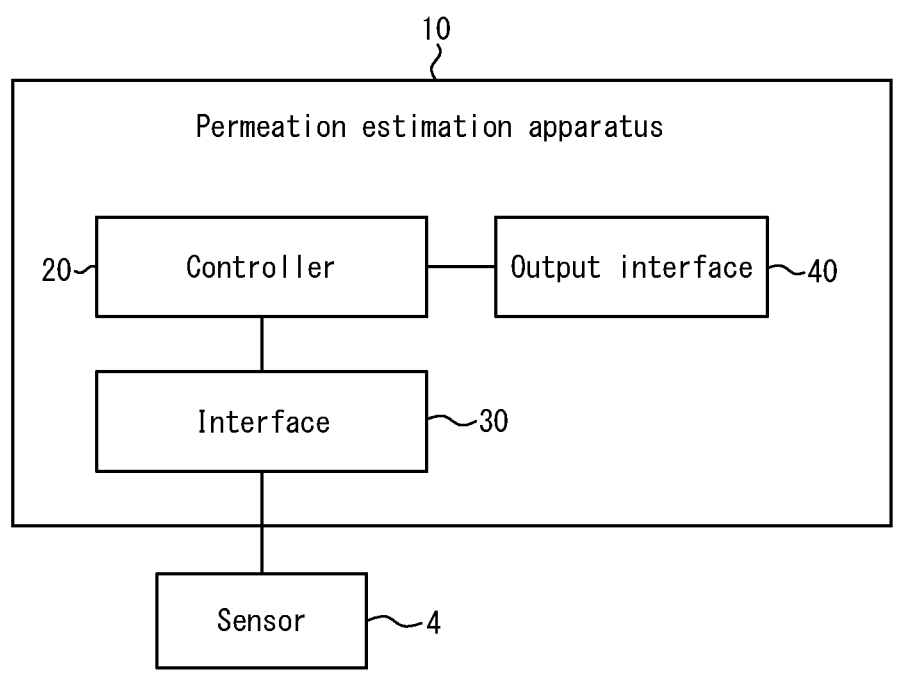
FIG. 2 is a diagram illustrating an example configuration of a permeation estimation apparatus according to an embodiment.

As illustrated in FIG. 2, the permeation estimation apparatus 10 includes a controller 20, an interface 30, and an output interface 40. The interface 30 is configured to be connectable to the sensor 4. The interface 30 may include a communication interface for a local area network (LAN) or the like. The interface 30 may communicably connect to the sensor 4 in a wired or wireless manner.

The controller 20 acquires measurement data of the sensor 4 via the interface 30. The controller 20 acquires information from the components of the permeation estimation apparatus 10 and controls the components. The controller 20 may be configured by a processor such as a central processing unit (CPU). The controller 20 may implement the various functions of the permeation estimation apparatus 10 by executing a predetermined program.

The controller 20 may include a memory. The memory may store various information used for operations of the controller 20, programs for implementing the functions of the controller 20, and the like. The memory may function as a working memory of the controller 20. The memory may, for example, be a semiconductor memory. The memory may be configured separately from the controller 20.

The output interface 40 outputs information acquired from the controller 20. The output interface 40 may notify a user of information by outputting visual information, such as characters, graphics, or images, directly or via an external apparatus or the like. The output interface 40 may include a display device and may be connected to the display device in a wired or wireless manner. The display device may include various types of displays, such as a liquid crystal display. The output interface 40 may notify the user of information by outputting audio information, such as sound, directly or via an external apparatus or the like. The output interface 40 may include an audio output device, such as a speaker, and may be connected to the audio output device in a wired or wireless manner. The output interface 40 may notify the user of information not only with visual information or audio information but also by outputting, directly or via an external apparatus or the like, information that the user is capable of perceiving with a different sense.

(Operations to Determine End of Soaking Process)

Figure 3:
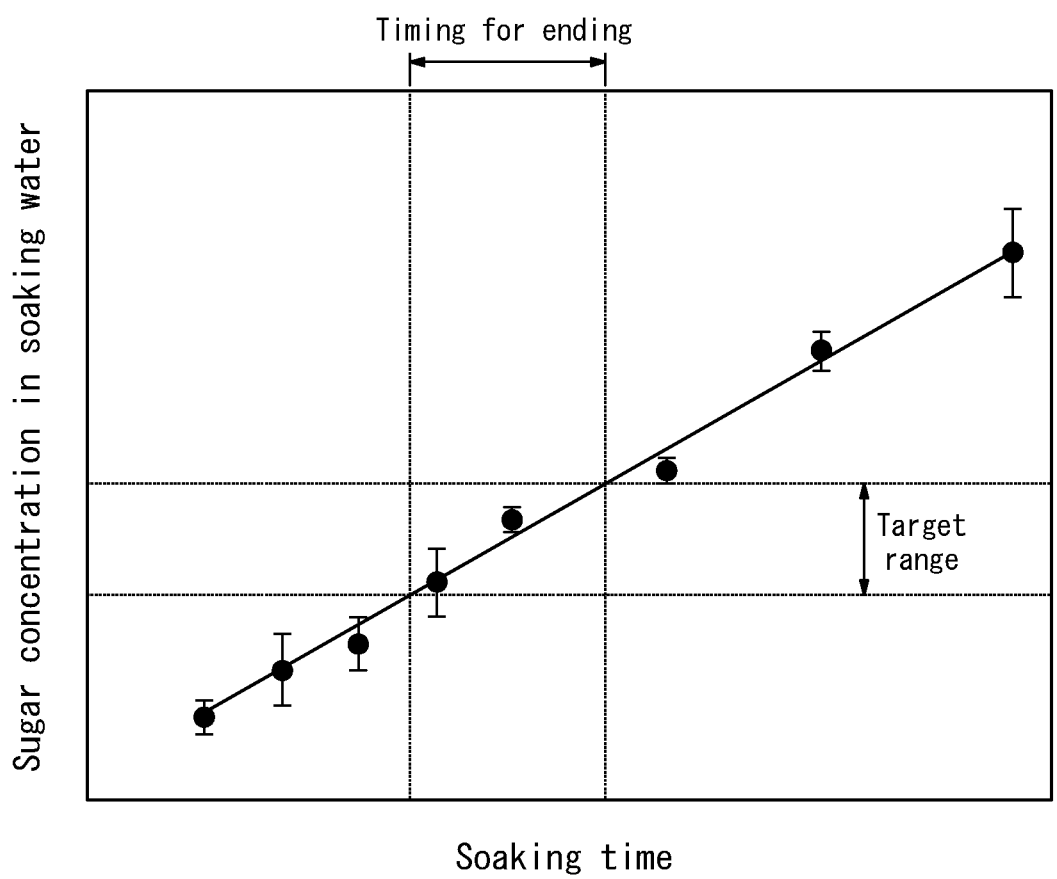
FIG. 3 is a graph illustrating an example relationship between soaking time and the concentration of a component eluted into the soaking solution.

As illustrated in FIG. 3, the results of an experiment indicate that the longer the soaked material 3 is soaked in the soaking solution 2, the higher the concentration of components of the soaked material 3 dissolved in the soaking solution 2. In the graph in FIG. 3, the horizontal axis represents the soaking time, and the vertical axis represents the sugar concentration in soaking water as the concentration of the component of the soaked material 3 dissolved in the soaking solution 2. A proportional relationship is observed between the concentration of the component of the soaked material 3 dissolved in the soaking solution 2 and the soaking time. The component concentration of the soaked material 3 in the soaking solution 2 is a numerical value that represents the eluted amount of a component of the soaked material 3. Elution of the components of the soaked material 3 occurs as a result of the soaking solution 2 penetrating the soaked material 3. Therefore, the component concentration of the soaked material 3 in the soaking solution 2 has the property of being an indicator of the degree of permeation of the soaking solution 2 into the soaked material 3. In other words, by clarifying in advance the relationship between the component concentration of the soaked material 3 in the soaking solution 2 and the degree of permeation of the soaking solution 2 into the soaked material 3, it is possible to estimate how much of the soaking solution 2 has permeated the soaked material 3 based on a measurement of the component concentration of the soaked material 3 in the soaking solution 2.

The controller 20 of the permeation estimation apparatus 10 acquires in advance the relationship between the degree of permeation of the soaking solution 2 in the soaked material 3 and the component concentration of the soaking solution 2 in the soaked material 3. The controller 20 may acquire the relationship between the concentration of each component and the degree of permeation. The controller 20 may, for example, acquire the relationship between the concentration of proteins in the soaking solution 2 and the degree of permeation. The controller 20 may, for example, acquire the relationship between the concentration of lipids in the soaking solution 2 and the degree of permeation.

The relationship between the degree of permeation and component concentration may be determined based on the results of an experiment conducted in advance. The relationship between the degree of permeation and component concentration may be expressed by a table or calibration curve, or by a relational expression. The relationship between the degree of permeation and component concentration differs according to the type of soaked material 3. For example, in the case of the soaked material 3 being soybeans, the relationship between the degree of permeation and the component concentration differs according to conditions such as the variety of soybean, the production area, or the harvest time. Therefore, the relationship between the degree of permeation and the component concentration may be prepared in advance for each condition. The table, calibration curve, or relational expression representing the relationship between the degree of permeation and the component concentration may include conditions, such as the variety of soybean, as parameters.

The controller 20 acquires the measurement results of the component concentration of the soaked material 3 in the soaking solution 2 from the sensor 4. The controller 20 can estimate the degree of permeation of the soaking solution 2 into the soaked material 3 based on the relationship between the degree of permeation and the component concentration and on the measurement results, acquired from the sensor 4, of the component concentration. The controller 20 determines that the timing for ending the soaking process has arrived in a case in which the estimated degree of permeation falls within a predetermined range. The predetermined range may be determined based on the results of experiments conducted in advance. The predetermined range differs according to the type of soaked material 3. For example, in the case of the soaked material 3 being soybeans, the predetermined range of appropriate timings for ending the soaking process differs according to conditions such as the variety of soybean, the production area, or the harvest time. Therefore, the predetermined range may be prepared in advance for each condition.

Based on the relationship between the degree of permeation and the component concentration, the controller 20 may calculate the range of component concentration of the soaked material 3 for which the degree of permeation falls within the predetermined range. The range of component concentration of the soaked material 3 for which the degree of permeation falls within the predetermined range is also referred to as the target range. The target range may be determined based on the results of experiments conducted in advance.

The controller 20 may determine whether the measured component concentration of the soaked material 3 is a value within the target range. The controller 20 may, for example, determine whether the lipid concentration in the soaking solution 2 is a value within the target range. The controller 20 may, for example, determine whether the protein concentration in the soaking solution 2 is a value within the target range. In a case in which the measured component concentration of the soaked material 3 is a value within the target range, the controller 20 may determine that the timing for ending the soaking process has arrived. In the example in FIG. 3, the target range of sugar concentration in the soaking water is represented as the range between two dashed lines extending along the horizontal axis. The possible timing for ending is represented as a range between two dashed lines extending along the vertical axis. The controller 20 may determine any timing between the two dashed lines extending along the vertical axis as the timing for ending.

In a case in which the controller 20 determines that the timing for ending the soaking process has arrived, the output interface 40 may report the result of the determination to the operator or manager of the soaking process.

In the soaking treatment system, the soaking process may start and end automatically. In this case, the controller 20 may output control information for ending the soaking process upon determining that the timing for ending the soaking process has arrived.

<Example Flowchart of Permeation Estimation Method>

Figure 4:
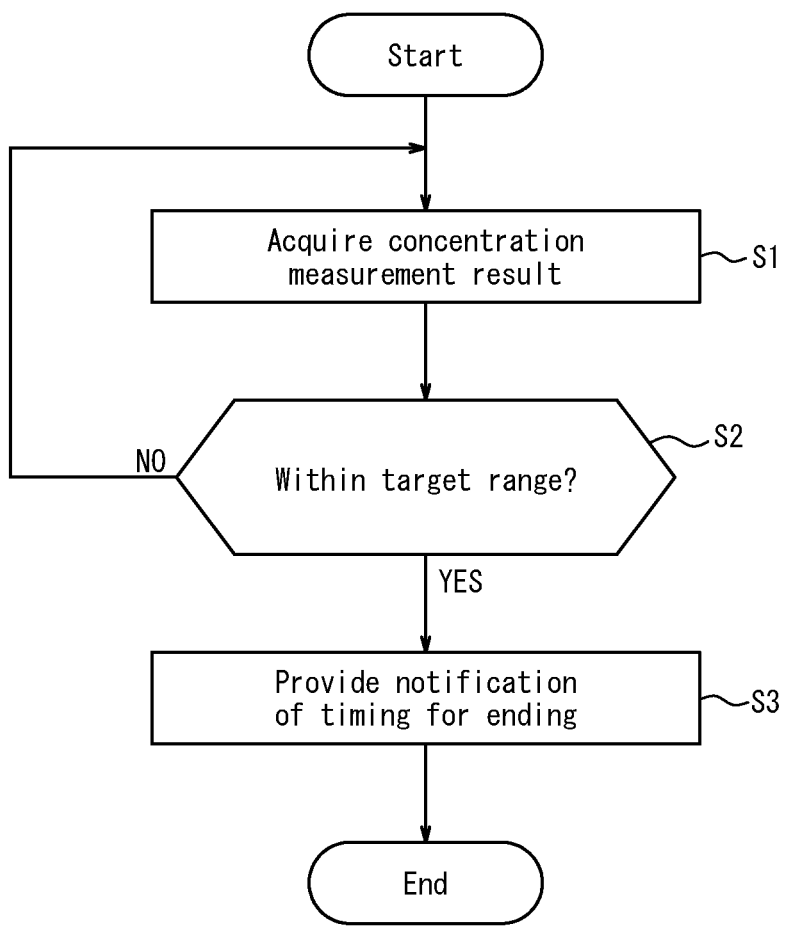
FIG. 4 is a flowchart illustrating example procedures for determining the end of soaking treatment.

The controller 20 of the permeation estimation apparatus 10 may execute a permeation estimation method that includes the procedures of the example flowchart in FIG. 4. The permeation estimation method may be implemented as a permeation estimation program executed by the processor of the controller 20 or the like. The permeation estimation program may be stored on a non-transitory computer readable medium.

The controller 20 acquires the concentration measurement results from the sensor 4 (step S1).

The controller 20 determines whether the component concentration is within the target range (step S2). Specifically, the controller 20 may determine whether the component concentration is within the target range for each component such as protein or lipids. The controller 20 may determine whether the concentration of all components dissolved in the soaking solution 2 is a value within the target range.

In a case in which the component concentration is not within the target range (step S2: NO), the controller 20 returns to the procedure of step S1. In a case in which the component concentration is within the target range (step S2: YES), the controller 20 determines that the timing for ending the soaking process has arrived and provides notification of the end timing (step S3). After completion of the procedure in step S3, the controller 20 ends execution of the procedures of the flowchart in FIG. 4.

The controller 20 may perform the procedure of estimating the degree of permeation based on the concentration measurement results before the procedure of step S2. In this case, the controller 20 may determine whether the estimated degree of permeation is within a predetermined range during the procedure in step S2. In a case in which the estimated degree of permeation is within the predetermined range, the controller 20 may proceed to the procedure of step S3 and determine that the timing for ending the soaking process has arrived.

According to the above-described soaking treatment system in the present embodiment, the progress of the soaking process is quantitatively evaluated. By the progress of the soaking process being evaluated quantitatively, the soaking treatment is completed in an appropriate time, without the soaked material 3 being left to soak for an excessively long time. In addition, completion of the soaking treatment in an appropriate length of time is expected to stabilize the quality of the processed product after the soaking treatment and reduce the risk that entire lots of the processed product will be discarded. Completion of the soaking treatment in an appropriate time also reduces the amount of wasted time during the soaking treatment. Also, use of the soaking solution 2 rather than the soaked material 3 to determine the timing for ending the soaking process reduces the loss of soaked material 3, which is the material for the processed product.

(Other Embodiments)

In the case of the soaked material 3 being soybeans, the controller 20 of the permeation estimation apparatus 10 may acquire, in advance, the relationship between the a property of soymilk, or raw soymilk obtainable after the soaking and grinding processes, and the degree of permeation of the soaking solution 2. The controller 20 may also acquire, in advance, the relationship between the property of raw soymilk or soymilk and the soaking time.

Figure 5:
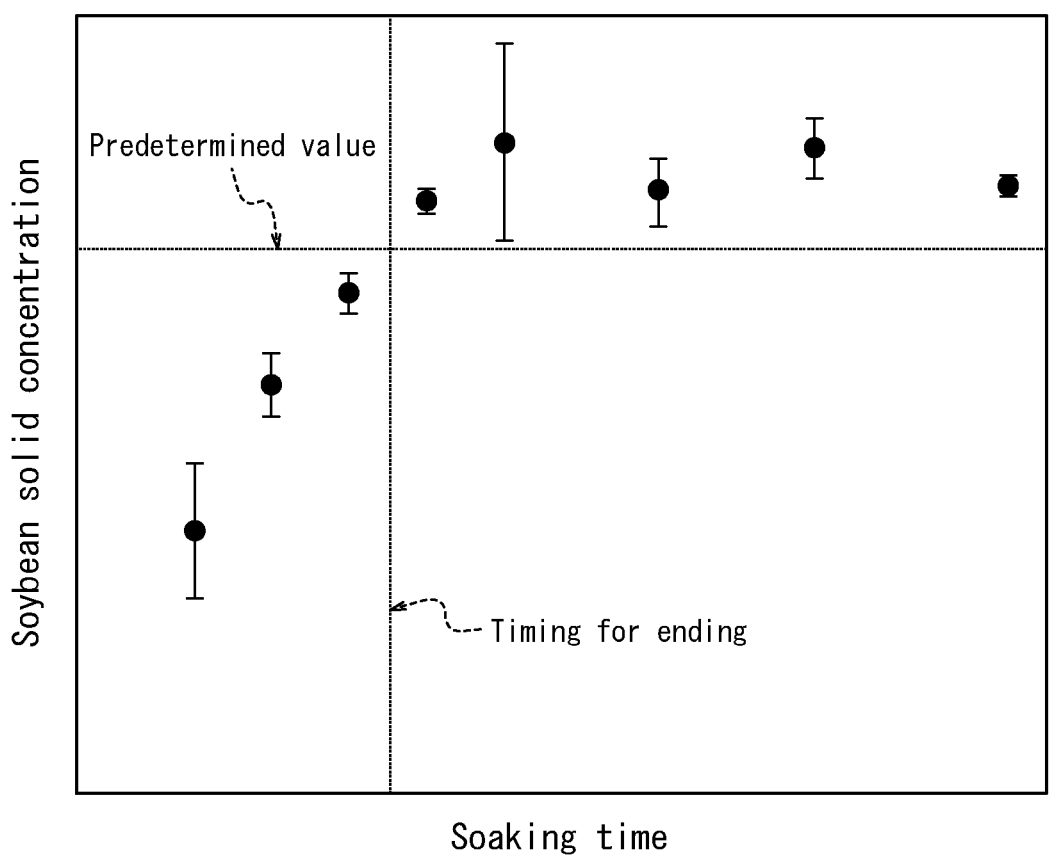
FIG. 5 is a graph illustrating an example relationship between soaking time and the soybean solid concentration of raw soymilk.

The property of raw soymilk or soymilk can, for example, be expressed as the solid concentration of raw soymilk. The controller 20 may acquire, in advance, the relationship between soaking time and the soybean solid concentration of raw soymilk, illustrated as a graph in FIG. 5. The horizontal axis in FIG. 5 represents soaking time, and the vertical axis represents the soybean solid concentration. The soybean solid concentration is calculated by dividing the dry weight of soybeans by the overall weight of the raw soymilk. The overall weight of the raw soymilk is calculated as the sum of the weight of the soybeans and the weight of the water. According to FIG. 5, the soaking time when the soybean solid concentration reaches the predetermined value represented by the dashed line extending along the horizontal axis may be determined as the timing for ending the soaking. In other words, based on a predetermined value as the target value of the soybean solid concentration of raw soymilk, the controller 20 may calculate the timing for ending the soaking so that the soaking time becomes an appropriate time.

Figure 6:
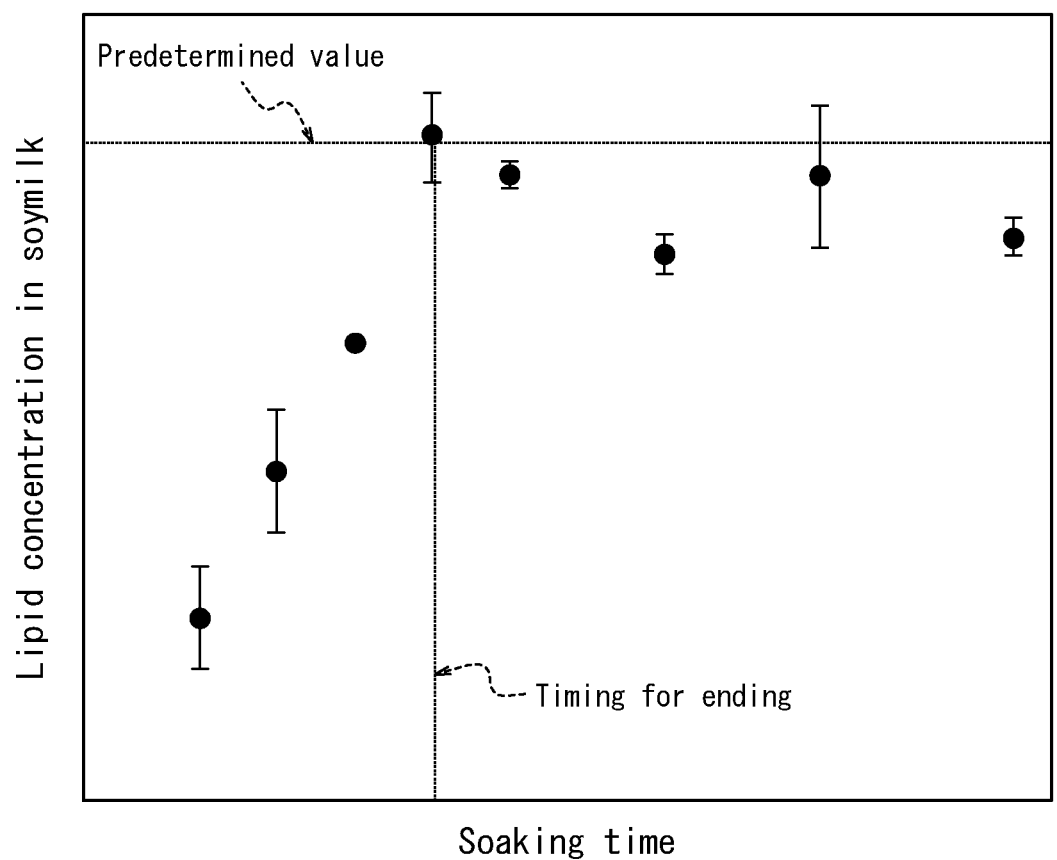
FIG. 6 is a graph illustrating an example relationship between soaking time and the lipid concentration in soymilk.

The property of raw soymilk or soymilk can, for example, be expressed as the lipid concentration in soymilk. The controller 20 may acquire, in advance, the relationship between soaking time and the lipid concentration in soymilk, illustrated as a graph in FIG. 6. The horizontal axis in FIG. 6 represents soaking time, and the vertical axis represents the lipid concentration. The lipid concentration is calculated by dividing the weight of lipids included in the soymilk by the overall weight of the soymilk. According to FIG. 6, the soaking time when the lipid concentration reaches the predetermined value represented by the dashed line extending along the horizontal axis may be determined as the timing for ending the soaking. In other words, based on a predetermined value as the target value of the lipid concentration in soymilk, the controller 20 may calculate the timing for ending the soaking so that the soaking time becomes an appropriate time.

Figure 7:
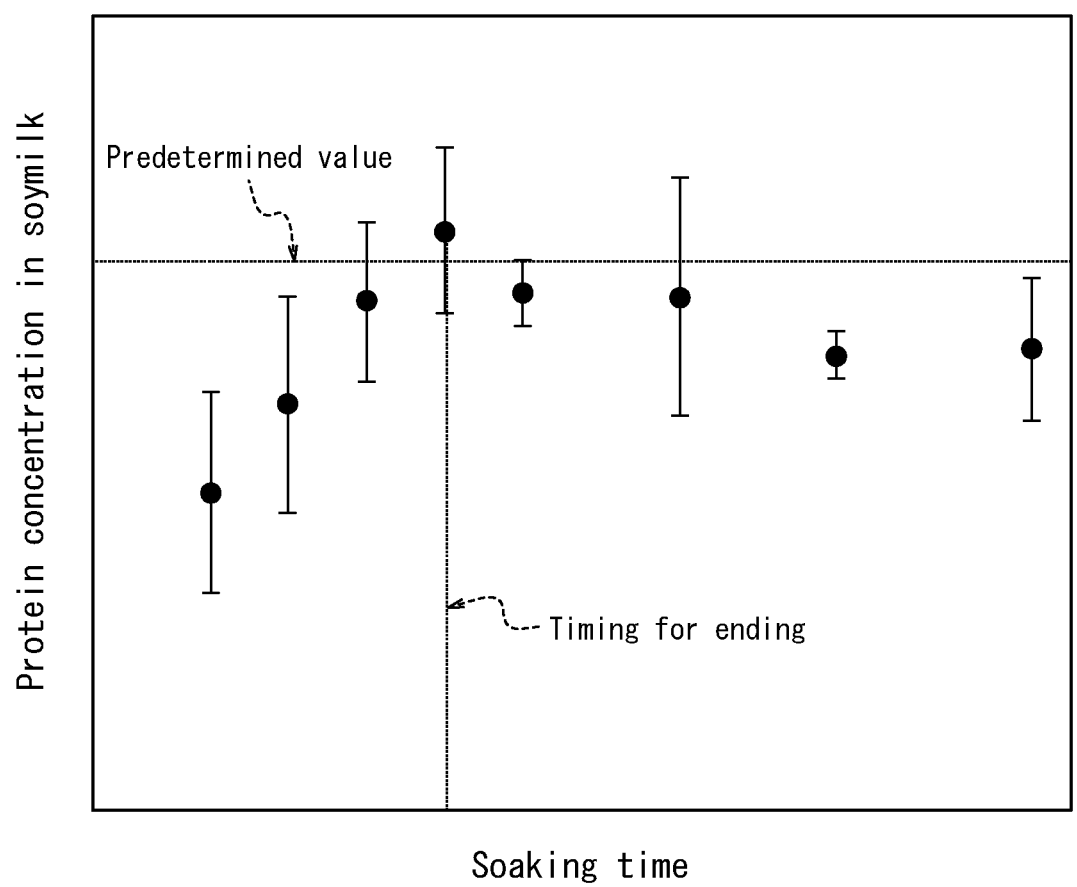
FIG. 7 is a graph illustrating an example relationship between soaking time and the protein concentration in soymilk.

The property of raw soymilk or soymilk can, for example, be expressed as the protein concentration in soymilk. The controller 20 may acquire, in advance, the relationship between soaking time and the protein concentration in soymilk, illustrated as a graph in FIG. 7. The horizontal axis in FIG. 7 represents soaking time, and the vertical axis represents the protein concentration. The protein concentration is calculated by dividing the weight of proteins included in the soymilk by the overall weight of the soymilk. According to FIG. 7, the soaking time when the protein concentration reaches the predetermined value represented by the dashed line extending along the horizontal axis may be determined as the timing for ending the soaking. In other words, based on a predetermined value as the target value of the protein concentration in soymilk, the controller 20 may calculate the timing for ending the soaking so that the soaking time becomes an appropriate time.

In this way, by acquiring the relationship between the degree of permeation or soaking time and the property of the raw soymilk or soymilk in advance, the controller 20 can estimate the property of the raw soymilk or soymilk after the soaking process but before the process of grinding the soybeans is conducted. The controller 20 can also estimate the quality of the final processed product. In this way, the timing for ending the soaking treatment is determined while taking into consideration the quality of the processed product. Consequently, the accuracy of estimating the timing for ending the soaking treatment is improved.

The controller 20 can also determine the timing for ending the soaking treatment in accordance with the target value of a property of the raw soymilk or soymilk. In other words, together with the target value of a property of the raw soymilk or soymilk, the controller 20 can calculate the target range that serves as the reference for determining, during the procedure in step S2 of the flowchart in FIG. 4, the concentration of the soybean component dissolved in the soaking solution 2. Together with the target value of a property of the raw soymilk or soymilk, the controller 20 can also calculate a predetermined range that serves as the reference for determining, during an alternative procedure for step S2 of the flowchart in FIG. 4, the estimated degree of permeation.

The controller 20 may determine the conditions for further processing of the soaked material 3 after the soaking process. Specifically, in the case of the soaked material 3 being soybeans, the controller 20 estimates a property of the raw soymilk based on the soybean component concentration in the soaking solution 2 and determines the processing conditions such that the property of the raw soymilk becomes the desired property. The processing conditions may, for example, include the amount of an additive added in the process of grinding soybeans. In other words, the controller 20 may calculate the amount of additive to be added in various post-processes, such as the grinding process, based on the soybean component concentration in the soaking solution 2. The additive may include water, for example, or other components. In this way, the controller 20 can adjust the quality of the processed product according to the condition of the soaked material 3 during the soaking process. Consequently, the predetermined range in which the treatment time for the soaking process is suitable time can be extended. In other words, the degree of freedom of the timing for ending the soaking treatment is increased.

Figure 8:
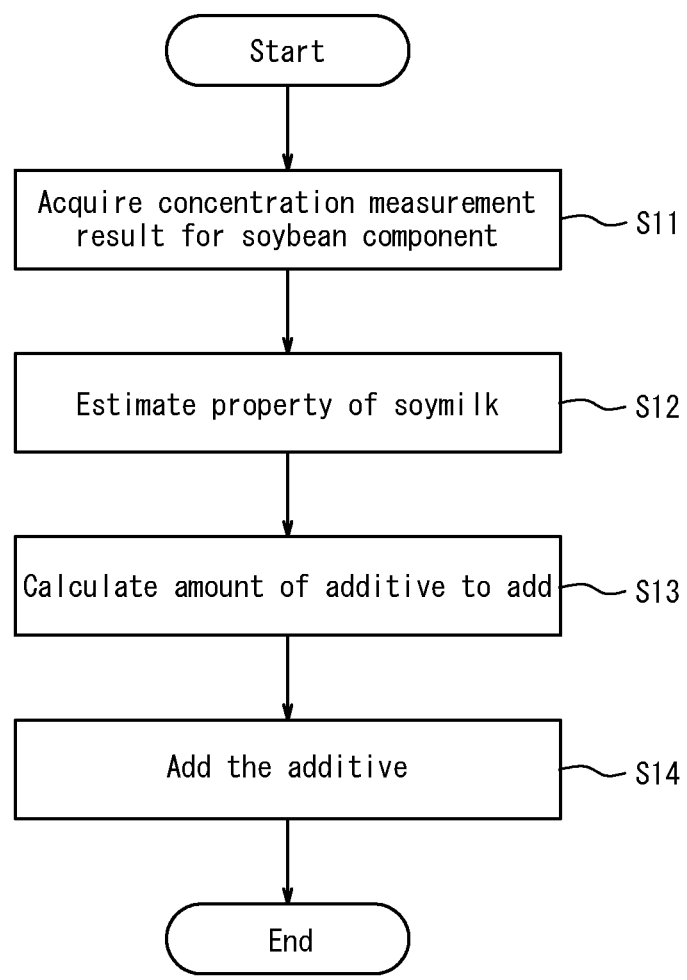
FIG. 8 is a flowchart illustrating example procedures for determining the processing conditions of a soaked material.

The controller 20 may execute an additive amount calculation method that includes the procedures of the example flowchart in FIG. 8. The additive amount calculation method may be implemented as an additive amount calculation program executed by the processor of the controller 20 or the like. The additive amount calculation program may be stored on a non-transitory computer readable medium. The soaked material 3 is assumed to be soybeans.

The controller 20 acquires the result of measuring the concentration of the soybean component in the soaking solution 2 from the sensor 4 (step S11).

The controller 20 estimates a property of the raw soymilk (step S12). Specifically, the controller 20 estimates a property of the raw soymilk based on the soybean component concentration in the soaking solution 2.

The controller 20 calculates the amount of additive to be added (step S13).

The post-process operator or apparatus adds the additive (step S14). The controller 20 outputs, to the post-process operator or apparatus, the amount of additive calculated in the procedure of step S13. After executing the procedure of step S14, the controller 20 ends execution of the procedures of the flowchart in FIG. 8.

Based on information on the quality of the processed product obtainable by the implementation of the post-process, the controller 20 may change the target range that serves as the reference for determining the concentration of the soybean component dissolved in the soaking solution 2 and/or the predetermined range that serves as the reference for determining the estimated degree of permeation. In other words, the controller 20 may feed information on the quality of the processed product back to the reference for determining the timing for ending the soaking treatment.

The operations and the permeation estimation method performed by the permeation estimation apparatus 10 according to the present disclosure can be employed in various manufacturing processes, not only in the soybean soaking process, in the case in which the soaked material 3 is soybeans. The various manufacturing processes may, for example, include food processing of soy milk, tofu, boiled soybeans, miso, or the like; processing of cosmetics, cooking oil, or fuel using soybean oil and fat; or material processing such as plastics using soy-derived proteins.

The operations and the permeation estimation method performed by the permeation estimation apparatus 10 according to the present disclosure are applicable not only to soybeans, but in general to the soaking treatment of soaked materials 3 such that a component of the soaked material 3 is a substance that dissolves in the soaking solution 2. For example, expected uses include the soaking process of beans such as adzuki beans or green peas, rice such as white rice or brown rice, paper pulp, and the like. In the case of the soaked material 3 being beans, the quality of the processed product, such as bean jam or boiled beans, can be improved. In the case of the soaked material 3 being rice, the quality of the processed product, such as sake, can be improved. In the case of the soaked material 3 being paper pulp, the quality of the paper can be improved. In the case of the soaked material 3 being carbon nanotubes or carbon nanofibers, the quality of the carbon products can be improved.

A permeation estimation program or a quality control program may be executed by a computer connected over a network. In other words, the permeation estimation apparatus 10 may be realized by cloud computing.

Although embodiments of the present disclosure have been described through drawings and examples, it is to be noted that various changes and modifications can be made by those skilled in the art on the basis of the present disclosure. Therefore, such changes and modifications are to be understood as included within the scope of the present disclosure. For example, the functions or the like included in the various components or steps may be reordered in any logically consistent way. Furthermore, components or steps may be combined into one or divided.

The invention claimed is:

1. A determination apparatus comprising:
    an interface configured to connect to a sensor that measures a concentration of a component of a soaked material soaked in a soaking solution, the component being eluted from the soaked material in the soaking solution; and
    a controller configured to acquire a measurement result of the concentration of the component from the interface and determine that a timing for ending a process of soaking the soaked material in the soaking solution has arrived when the measurement result of the concentration of the component is a value within a target range.

2. The determination apparatus according to claim 1, wherein based on the measurement result of the concentration of the component, the controller is configured to estimate a quality of a processed product obtainable by processing the soaked material, wherein the quality of the processed product includes a solid concentration of raw soymilk when the soaked material is soybeans.

3. The determination apparatus according to claim 2, wherein based on the measurement result of the concentration of the component, the controller is configured to determine a processing condition of the soaked material in a process subsequent to a soaking process, wherein the processing condition includes an amount of additive to be added in the process subsequent to the soaking process.

4. The determination apparatus according to claim 1, wherein based on the measurement result of the concentration of the component, the controller is configured to determine a processing condition of the soaked material in a process subsequent to a soaking process, wherein the processing condition includes an amount of additive to be added in the process subsequent to the soaking process.

5. A determination method comprising:
    acquiring a measurement result of a concentration of a component of a soaked material soaked in a soaking solution from a sensor that measures the concentration of the component, the component being eluted from the soaked material in the soaking solution; and
    determining that a timing for ending a process of soaking the soaked material in the soaking solution has arrived when the measurement result of the concentration of the component is a value within a target range.

6. The determination method according to claim 5, further comprising, based on the measurement result of the concentration of the component, estimating a quality of a processed product obtainable by processing the soaked material, wherein the quality of the processed product includes a solid concentration of raw soymilk when the soaked material is soybeans.

7. The determination method according to claim 6, further comprising, based on the measurement result of the concentration of the component, determining a processing condition of the soaked material in a process subsequent to a soaking process, wherein the processing condition includes an amount of additive to be added in the process subsequent to the soaking process.

8. The determination method according to claim 5, further comprising, based on the measurement result of the concentration of the component, determining a processing condition of the soaked material in a process subsequent to a soaking process, wherein the processing condition includes an amount of additive to be added in the process subsequent to the soaking process.

\* \* \* \* \*